(12) United States Patent
Jeong et al.

(10) Patent No.: US 9,503,624 B2
(45) Date of Patent: Nov. 22, 2016

(54) OPTICAL IMAGING SYSTEM USING MULTIPLE LIGHT SOURCES AND DRIVING CONTROL METHOD THEREOF

(71) Applicant: Electronics and Telecommunications Research Institute, Daejeon (KR)

(72) Inventors: Eun-Ju Jeong, Daejeon (KR); Bong Kyu Kim, Daejeon (KR); Won Ick Jang, Daejeon (KR); Chang-Geun Ahn, Daejeon (KR); Hyun Woo Song, Daejeon (KR)

(73) Assignee: ELECTRONICS AND TELECOMMUNICATIONS RESEARCH INSTITUTE, Daejeon (KR)

( * ) Notice: Subject to any disclaimer, the term of this patent is extended or adjusted under 35 U.S.C. 154(b) by 323 days.

(21) Appl. No.: 14/198,768

(22) Filed: Mar. 6, 2014

(65) Prior Publication Data

US 2014/0285648 A1 Sep. 25, 2014

(30) Foreign Application Priority Data

Mar. 20, 2013 (KR) .................. 10-2013-0029948
Aug. 29, 2013 (KR) .................. 10-2013-0103233

(51) Int. Cl.
 *A61B 5/00* (2006.01)
 *H04N 5/225* (2006.01)
 *H04N 5/232* (2006.01)
 (Continued)

(52) U.S. Cl.
 CPC ........ *H04N 5/2256* (2013.01); *G01N 21/6456* (2013.01); *H04N 5/23229* (2013.01); *H04N 5/332* (2013.01)

(58) Field of Classification Search
 CPC ............... A61B 5/0071; A61B 1/043; G01N 21/6456; G01N 21/6486; F21W 2131/205; G06T 2207/10048; H04N 5/2256

USPC .......... 348/77; 250/226; 600/317, 431, 476; 436/172

See application file for complete search history.

(56) References Cited

U.S. PATENT DOCUMENTS 5,508,741 A * 4/1996 Hieda .................... H04N 5/208
 348/252
2004/0225222 A1 * 11/2004 Zeng ..................... A61B 1/043
 600/476

(Continued)

OTHER PUBLICATIONS

Alec M. De Grand et al., "An Operational Near-Infrared Fluorescence Imaging System Prototype for Large Animal Surgery", Technology in Cancer Research & Treatment ISSN 1533-0346, vol. 2, No. 6, Dec. 2003.

*Primary Examiner* — Sath V Perungavoor
*Assistant Examiner* — Nathnael Aynalem
(74) *Attorney, Agent, or Firm* — Rabin & Berdo, P.C.

(57) ABSTRACT

Provided is an optical imaging system capable of increasing diagnosis reliability and preciseness, and efficiently observing a target. The optical imaging system using multiple light sources according to an embodiment of the present invention includes a first light source generating a first light modulated with a first frequency, a second light source generating a second light modulated with a second frequency, a camera simultaneously detecting multiple lights output from an object after the first and second lights are illuminated on the object and outputting multiple image detecting signals, and an image processing unit processing the multiple image detecting signals to obtain a first image representing a shape of the object and a second image representing a desired target portion of the object.

18 Claims, 5 Drawing Sheets

(51) Int. Cl.
  *H04N 5/33* (2006.01)
  *G01N 21/64* (2006.01)

(56) References Cited

U.S. PATENT DOCUMENTS

| | | | | |
|---|---|---|---|---|
| 2005/0182321 A1* | 8/2005 | Frangioni | .......... | A61B 1/00186 600/431 |
| 2007/0203413 A1* | 8/2007 | Frangioni | .............. | A61B 5/415 600/478 |
| 2008/0103390 A1* | 5/2008 | Contag | .................. | A61B 19/52 600/427 |
| 2009/0066787 A1* | 3/2009 | Yamazaki | ............ | A61B 1/0638 348/70 |
| 2009/0236541 A1* | 9/2009 | Lomnes | ................. | A61B 1/043 250/458.1 |
| 2009/0268010 A1* | 10/2009 | Zhao | .................. | A61B 1/00009 348/45 |
| 2010/0245551 A1* | 9/2010 | Morita | ............... | A61B 1/00009 348/68 |
| 2010/0245616 A1* | 9/2010 | Yoshino | ............... | A61B 1/0638 348/223.1 |
| 2011/0261175 A1* | 10/2011 | Fomitchov | .......... | A61B 5/0071 348/61 |
| 2011/0270092 A1* | 11/2011 | Kang | ................. | A61B 5/0071 600/476 |

\* cited by examiner

OPTICAL IMAGING SYSTEM USING MULTIPLE LIGHT SOURCES AND DRIVING CONTROL METHOD THEREOF

CROSS-REFERENCE TO RELATED APPLICATIONS

This U.S. non-provisional patent application claims priority under 35 U.S.C. §119 of Korean Patent Application No. 10-2013-0029948, filed on Mar. 20, 2013, and Korean Patent Application No. 10-2013-0103233, filed on Aug. 29, 2013, the entire contents of which are hereby incorporated by reference.

BACKGROUND OF THE INVENTION

The present invention disclosed herein relates to image processing of optical imaging medical equipment, and more particularly, to an optical imaging system using multiple light sources and a driving control method thereof.

Typically in order to find a location of a target, a fluorescence imaging technology which images a fluorescence signal output after injecting a fluorescence substance is widely used.

The fluorescence imaging technology is a technique which images a light emitted after exciting fluorescence materials in a body by using a high energy ray. When the fluorescence imaging technology is applied to a human body, changes of cells inside and outside the body can be observed in a non-invasively manner in real time. Accordingly, the fluorescence imaging technology is used in various researches on a human body and diagnoses on diseases.

Such a fluorescence imaging technology has recently evolved into a level of obtaining and imaging fluorescence in a near-infrared region in order to obtain an image for a point deep inside the object's body by raising penetrance, in addition to obtaining and imaging fluorescence in an ultraviolet range or a visible ray range.

Tracking a target is easy in a fluorescence imaging system. However, a fluorescence signal is greatly affected by surrounding lights, because it is relatively weak compared to a general signal. Accordingly, since a dark environment is necessary for fluorescence-imaging, there is the limitation in that sufficient lights are not provided for operation.

In addition to observation for a shape of an object in order to figure out a precise location of a target in the object, a technology for processing a fluorescence image is necessary for precisely confirming the location of the target, while providing an optimal operation environment.

SUMMARY OF THE INVENTION

The present invention provides an optical imaging system using multiple light sources and a driving control method thereof.

The present invention also provides an optical imaging system capable of outputting a fluorescence image and a general color image on one screen for further reliable diagnosis.

The present invention also provides an optical imaging system capable of simultaneously observing a general image and a fluorescence image by using a single optical system in order to increase precision of a target location.

Embodiments of the present invention provide optical imaging systems using multiple light sources, including: a first light source generating a first light modulated with a first frequency; a second light source generating a second light modulated with a second frequency; a camera simultaneously detecting multiple lights output from an object after the first and second lights are illuminated on the object and outputting multiple image detecting signals; and an image processing unit processing the multiple image detecting signals to obtain a first image representing a shape of the object and a second image representing a desired target portion of the object.

In other embodiments of the present invention, optical imaging systems using multiple light sources, include: a first light source generating a white light modulated with a first frequency; a second light source generating a fluorescence light modulated with a second frequency, which is different from the first frequency; a charge coupler device camera simultaneously detecting multiple lights output from an object after the white light and the fluorescence light are illuminated on the object and outputting multiple image detecting signals; and a digital signal processing unit for separating, from the multiple image detecting signals, a first image representing a shape or distribution of the object and a second image representing a desired target portion of the object.

In still other embodiments of the present invention, driving control methods of an optical imaging system using multiple light sources, include: illuminating an object with a white light modulated with a first frequency to obtain a first emission light; inputting the first emission light to a single camera to generate a first image detecting signal; obtaining a first image representing a shape or distribution of the object from the first image detecting signal; illuminating the object with a fluorescence light modulated with a second frequency which is different from the first frequency to obtain a second emission light; simultaneously detecting multiple emission lights that the first and second emission lights are merged through the single camera to generate multiple image detecting signals; and separating, from the multiple image detecting signals, the first image representing a shape or distribution of the object and the second image representing a desired target portion of the object.

BRIEF DESCRIPTION OF THE DRAWINGS

The accompanying drawings are included to provide a further understanding of the present invention, and are incorporated in and constitute a part of this specification. The drawings illustrate exemplary embodiments of the present invention and, together with the description, serve to explain principles of the present invention. In the drawings.

DETAILED DESCRIPTION OF PREFERRED EMBODIMENTS

Figure 1:
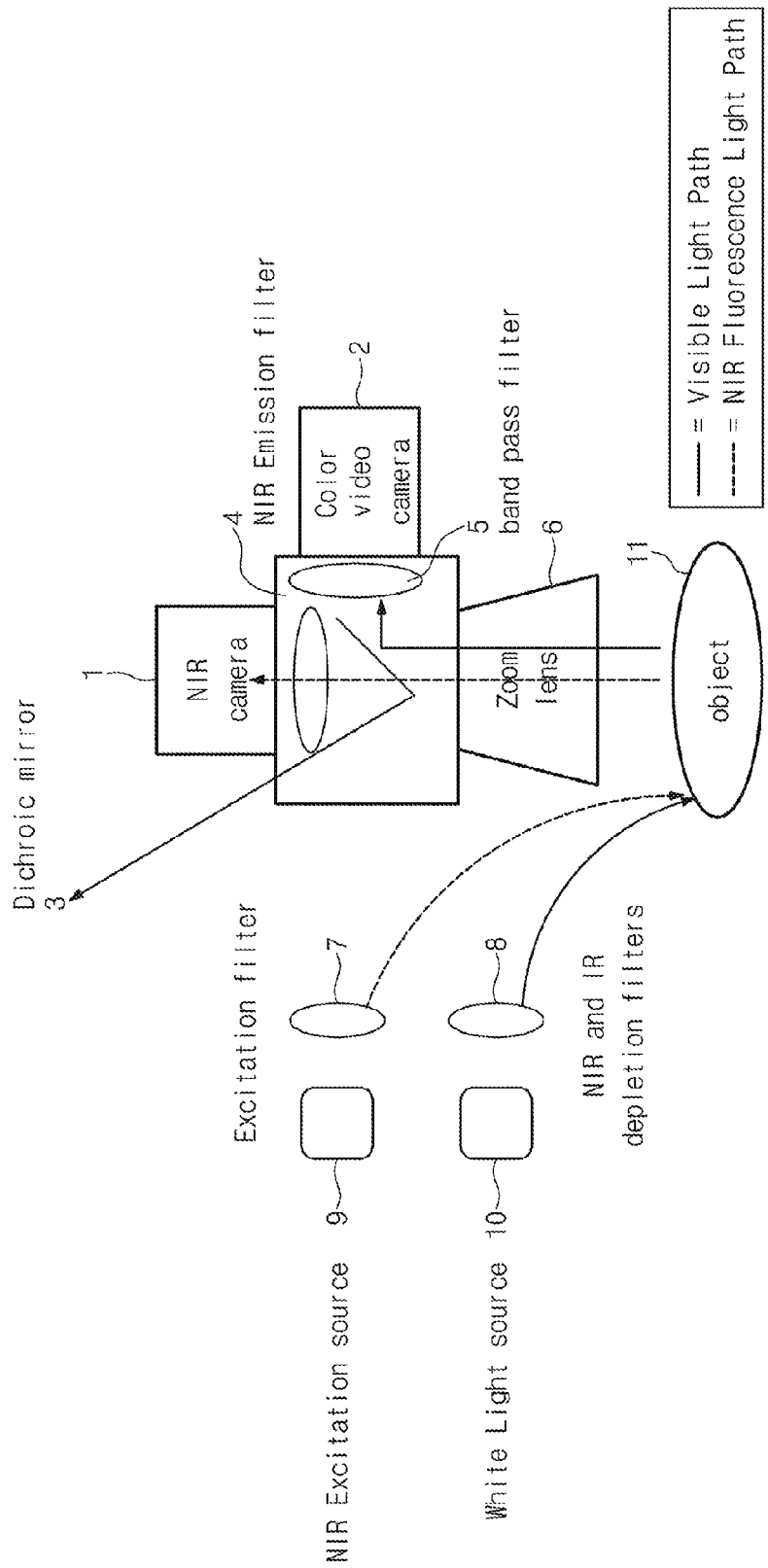
FIG. 1 is a schematic diagram of a typical imaging system using multiple light sources.

Preferred embodiments of the present invention will be described below in more detail with reference to the accompanying drawings. The present invention may, however, be embodied in different forms and should not be constructed as limited to the embodiments set forth herein. Rather, these embodiments are provided so that this disclosure will be thorough and complete, and will fully convey the scope of the present invention to those skilled in the art.

In the present disclosure, if certain devices or lines are described as being connected to a target device block, they are not only directly connected to the target device block, but also connected to the target device block by means of any other device.

Also, the same or similar reference numerals provided in each drawing denote the same or similar components. In some drawings, connection relations between devices and lines are merely shown for efficient description of the technical spirit, and therefore other devices or circuit blocks may be further provided.

Exemplary embodiments set forth herein may include complementary embodiments thereof, and it will be noted that a general operation and properties of an optical imaging system using multiple light sources may be omitted so as not to obscure the essential point of the present invention.

Hereinafter, it will be described about an exemplary embodiment of the present invention in conjunction with the accompanying drawings.

FIG. 1 is a schematic diagram illustrating a typical imaging system using multiple light sources.

Referring to FIG. 1, lights output from a fluorescence light source 9 and a white light source 10 respectively pass a fluorescence filter 7 and an infrared depletion filter 8 having respective corresponding wavelength bands and illuminate a target 11, which is an object. The object 11 absorbs a specific wavelength light and emits a fluorescence light having a wavelength unique to the object. The emitted fluorescence light is collected through a zoom lens 6 and incident to low-pass near infrared (NIR) emission filter 4 which may pass only a fluorescence wavelength. An NIR camera 1 receives a filter output from the low-pass NIR emission filter 4 and obtains a fluorescence image. Moreover, the white light is incident to a band pass filter 5 which blocks a fluorescence-related light and passes only a visible light, and a color video camera 2, which receives an output of the band pass filter 5, obtains a general image.

In a case of the imaging system of FIG. 1, it can be known that two cameras are used for simultaneously obtaining a fluorescence image signal and a general image signal.

Figure 2A:
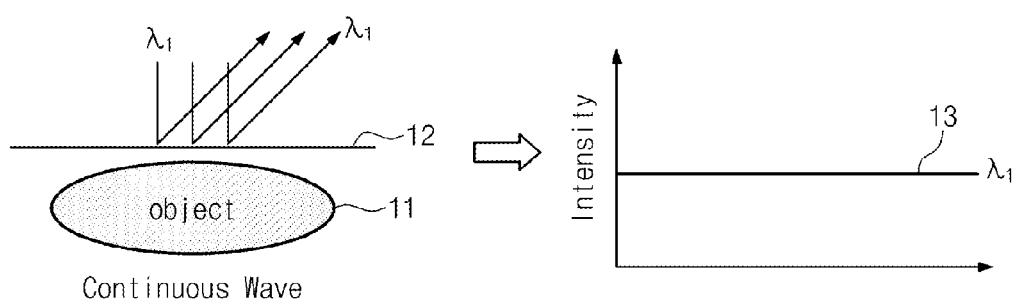
FIGS. 2A and 2B illustrate characteristics of a white light and a fluorescence light.
Figure 2B:
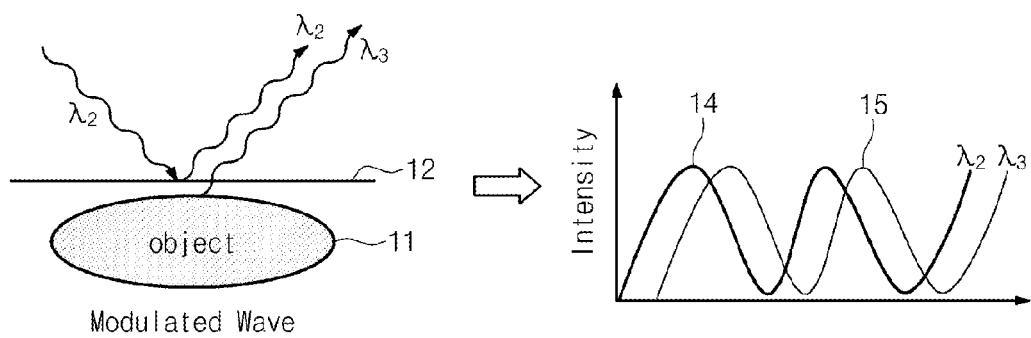

FIGS. 2A and 2B illustrate characteristics of a white light and a fluorescence light.

FIG. 2A illustrates a case where a continuous wave (CW) white light is used for a general image and FIG. 2B illustrates a case where a modulated light is used for a fluorescence image. In FIGS. 2A and 2B, horizontal axes of the graphs denote time and vertical axes denote intensities of the lights.

In FIG. 2A, when the CW white light ($\lambda_1$) is illuminated on the object 11, the light is reflected on the surface 12 of the object 11 and continuously emitted in a constant intensity. Thus, there is almost no change in intensity as shown in a graph 13.

In addition, FIG. 2B illustrates output characteristics in a case where a modulated wave is used as a fluorescence light for separating a fluorescence image from the general image. An optical signal absorbed and then output by the object 11 becomes a fluorescence image signal and a light of a wavelength 14 reflected on the surface 12 operates as a noise. A waveform of the light due to the modulated wave is represented as waveforms 14 and 15 in a graph of FIG. 2B.

Accordingly, in order to obtain only the fluorescence image, it is necessary to remove wavelength ($\lambda_2$) 14 among modulated wavelengths reflected on the surface 12.

Figure 3:
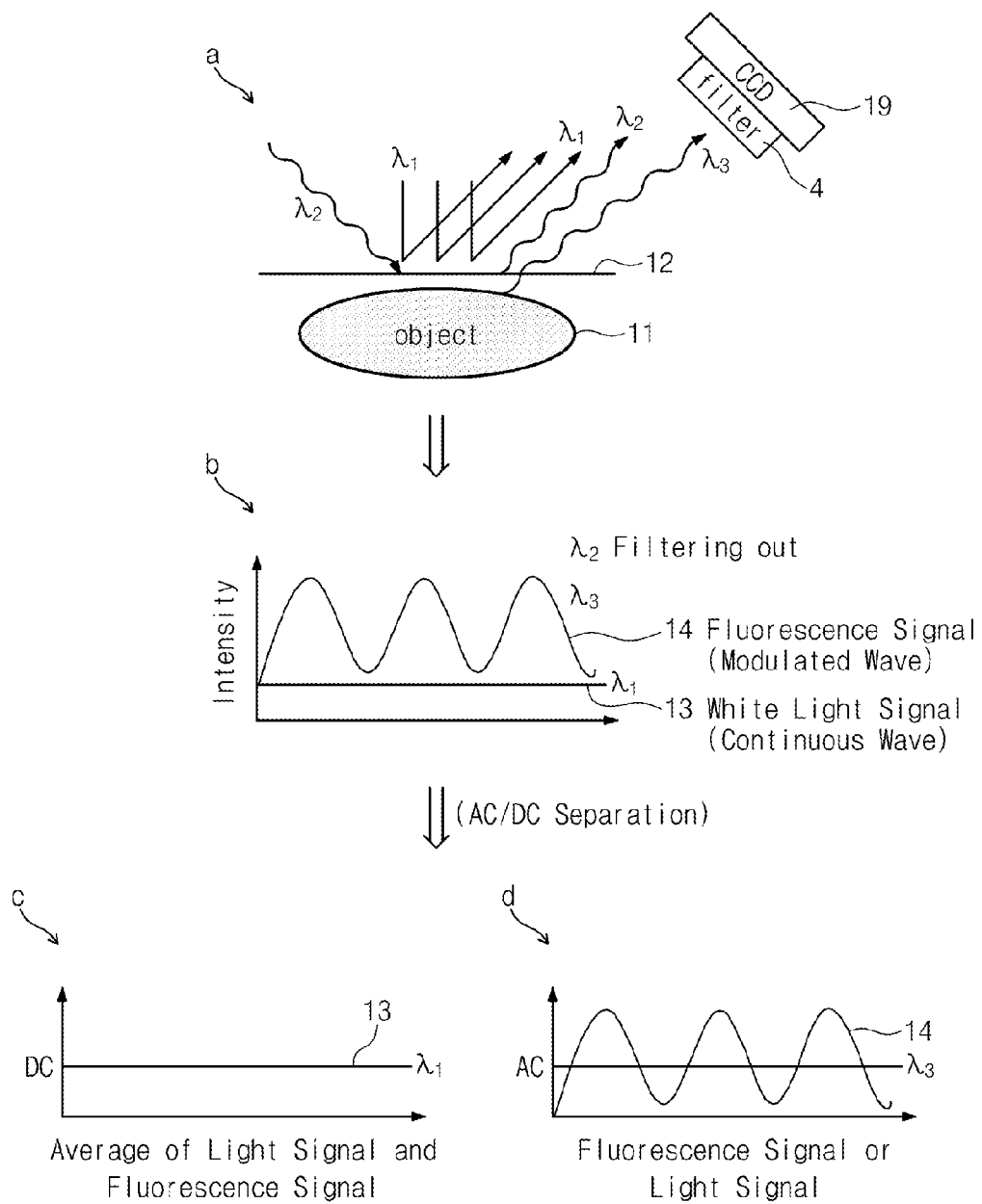
FIG. 3 illustrates a concept that a white light signal and a fluorescence signal are separated according to an embodiment of the present invention.

FIG. 3 illustrates a concept for separating a white light signal and a fluorescence signal according to an embodiment of the present invention.

As shown in FIG. 3(a), an excitation light and a white light are simultaneously incident to the object 11, and a continuous light ($\lambda_1$) of the white light, a reflection light ($\lambda_2$) due to the excitation light ($\lambda_2$), and a fluorescence light ($\lambda_3$) are emitted from the object 11. At this time, the reflection light ($\lambda_2$) due to the excitation light is filtered through an optical filter 4 and data is obtained through a charge coupled device (CCD) camera 19.

This data is digitalized by using an analog-to-digital converter (ADC) 16, and the digitalized data may be separated into an AC component signal and a DC component signal in a software manner as shown in FIGS. 3(c) and 3(d). Accordingly, a general image and a fluorescence image are respectively obtained from the separated signals.

Figure 4:
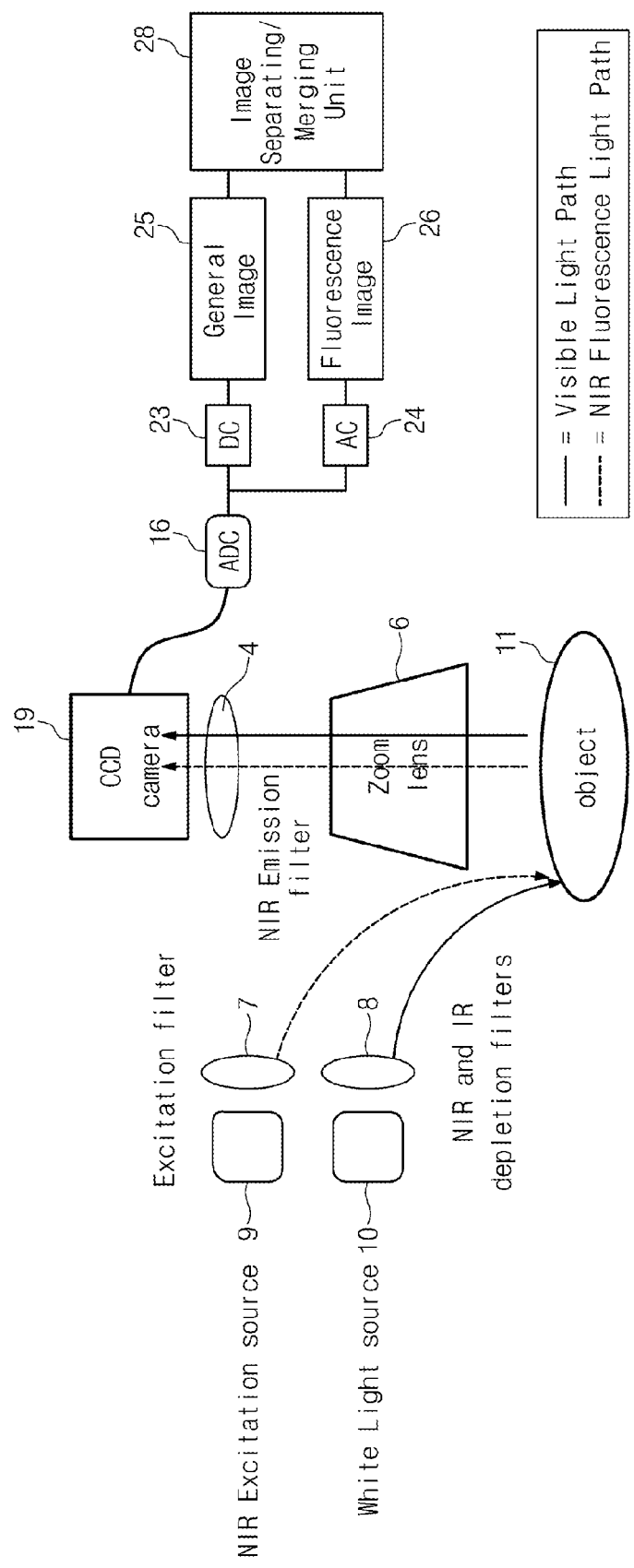
FIG. 4 is a block diagram illustrating an optical imaging system using multiple light sources according to an embodiment of the present invention.

FIG. 4 is a block diagram illustrating an optical imaging system using multiple light sources according an embodiment of the present invention.

Referring to FIG. 4, the optical imaging system using multiple light sources includes a first light source 10 generating a first light, which is modulated with a first frequency, and a second light source 9 generating a second light which is modulated with a second frequency.

Also, the optical imaging system further includes a single camera 19, which simultaneously detects multiple lights emitted from the object 11 after the first and second lights are illuminated on the object 11 and outputs multiple image detecting signals, and an image processing unit 16, 23, 24 and 28 which processes the multiple image detecting signals to obtain a first image (the general image) representing a shape of the object 11 and a second image (fluorescence image) representing a desired target portion of the object 11.

In FIG. 4, information on lights obtained from the multiple light sources is converted into digital data through the ADC 16 and separated into the AC component signal 24 and the DC component signal 23.

The DC component signal 23 is represented as the general image through low-pass-filtering, and the AC component signal 24 is represented as the fluorescence image through band-pass-filtering.

Here, the shape or distribution of the object 11 may be known through the general image, and a desired precise target may be confirmed through the fluorescence image.

In addition, since a merged image that the two images output from the camera 19 are merged is formed through an image separating/merging unit 28 which operates as an image merging unit, reliable information on the target may be obtained. Furthermore, the fluorescence image has a very smaller amplitude compared to the general image. Accordingly, when the fluorescence image signal is amplified, usability or utility may be increased.

Figure 5:
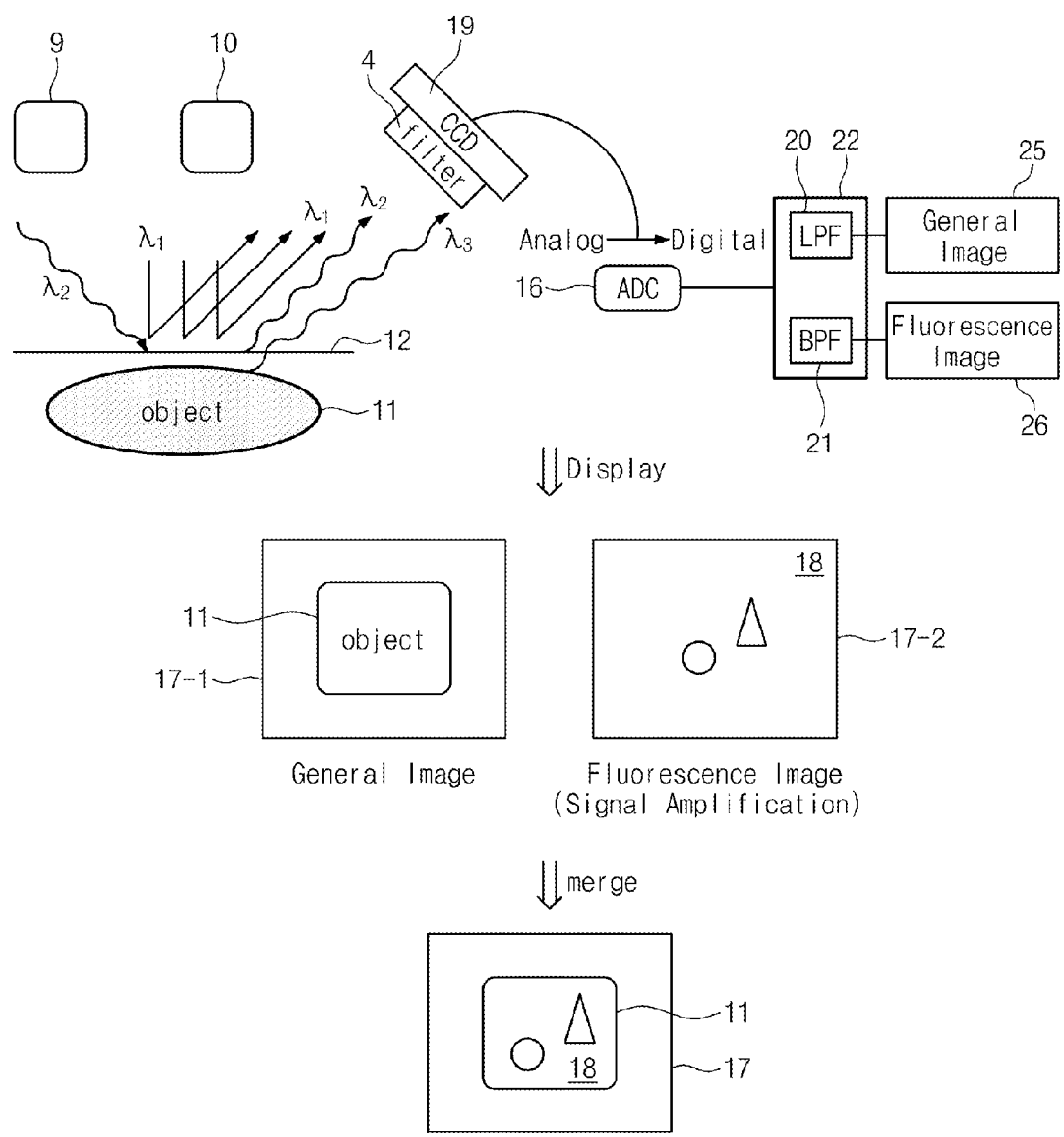
FIG. 5 is a block diagram illustrating an optical imaging system using multiple light sources according to another embodiment of the present invention.

FIG. 5 is a block diagram illustrating an optical imaging system using multiple light sources according to another embodiment of the present invention.

Referring to FIG. 5, the optical imaging system using multiple light sources includes a first light source 10 generating a white light, which is modulated with a first frequency, and a second light source 9 generating a fluorescence light, which is modulated with a second frequency.

In FIG. 5, the optical imaging system also includes a CCD camera 19 which simultaneously detects multiple lights emitted from the object 11 after the first and second lights are illuminated on the object 11 and outputs multiple image detecting signals, and a digital signal processing (DSP) unit 22 for separating the multiple image detecting signals into a first image (a general image) representing a shape or distribution of the object 11 and a second image (a fluorescence image) representing a desired target portion of the object 11.

In FIG. 5, in order to figure out existence and a location of the object 11, observation for the general image can be primarily performed by using a white light source 10.

During the general image observation, the light 10 from the white light source is illuminated on a diagnosis portion of the object 11. A light reflected by the diagnosis portion passes through the optical filter 4 and is directly provided as an input of the color CCD camera 19. Accordingly, a general image 17-1 with standard color is obtained from a low pass filter (LPF) 20 of the DSP unit 22.

When it is determined that a target is difficult to precisely observe through the observation of the general image 17-1 by means of the white light 10, the object 11 may be observed by using a fluorescence signal excited by a NIR modulated wave 9. At this time, each signal obtained through the single camera 19 is digitalized through the ADC 16 and output as the general image and the fluorescence image through the LPF 20 and a band pass filter (BPF) 21.

In the end, the general image 17-1 is obtained through the LPF 20 which performs low-pass-filtering in the DSP unit 22, and the fluorescence image 17-2 is obtained through the BPF 21 which performs band-pass-filtering.

Here, the shape and distribution of the object 11 may be known through the general image 17-1 and a desired precise target 18 may be confirmed through the fluorescence image 17-2.

In addition, since a merged image 17 that the two images 11 and 18 are merged may be formed through a single camera, reliable information on the object 11 can be obtained. Moreover, the fluorescence image has a very smaller signal amplitude compared to the general image. Accordingly, when the fluorescence image signal is amplified, usability or utility may be increased.

As described above, simple and precise mapping to a tracker is enabled by using two optical modes with one camera.

In addition, a target can be precisely diagnosed by using fluorescence light having a wide wavelength range. Also, since a general image, which is a background of a diagnosed portion, can be simultaneously provided on the basis of a reflection light of an excitation light, precise observation for the diagnosed portion is enabled.

According to the embodiments of the present invention, a location, a size, and a degree of metastasis of a target can be precisely and reliably identified by observing and analyzing a fluorescence image and a general image. Accordingly, a side effect can be minimized, since an operation range is selected on the basis of the precise and reliable information.

In addition, a target can be diagnosed by using an excitation light which has a wide wavelength range, and a color image, which becomes a background of a diagnosed portion, is also provided simultaneously with a fluorescence image. Accordingly, a doctor can precisely observe the diagnosed portion and precisely identify the location and the degree of metastasis of the target. Therefore, information is provided for enabling the target to be precisely and efficiently removed.

The above-disclosed object matter is to be considered illustrative, and not restrictive, and the appended claims are intended to cover all such modifications, enhancements, and other embodiments, which fall within the true spirit and scope of the present invention. Thus, to the maximum extent allowed by law, the scope of the present invention is to be determined by the broadest permissible interpretation of the following claims and their equivalents, and shall not be restricted or limited by the foregoing detailed description.

What is claimed is:

1. An optical imaging system using multiple light sources, comprising:
    a first light source generating a first light modulated with a first frequency;
    a second light source generating a second light modulated with a second frequency;
    a camera simultaneously detecting multiple lights output from an object after the first and second lights are illuminated on the object and outputting multiple image detecting signals the multiple image detecting signals including a first reflection light of the first light that is reflected on a surface of the object, a second reflection light of the second light that is reflected on said surface of the object, and a third reflection light of the second light that is reflected on a desired target portion inside the object;
    a filter for removing the second reflection light from the multiple image detecting signals after detection by the camera; and
    an image processing unit processing the multiple image detecting signals without the removed second reflection light to obtain a first image representing a shape of the object from the first reflection light and a second image representing the desired target portion inside the object from the third reflection signal.

2. The optical imaging system of claim 1, wherein the first light is a continuous wave light.

3. The optical imaging system of claim 2, wherein the second light is a fluorescence light.

4. The optical imaging system of claim 1, wherein the image processing unit comprises:
    an analog-to-digital converter converting the multiple image detecting signals into digital data;
    a low pass filter low-pass-filtering the digital data to output as the first image;
    a band pass filter band-pass-filtering the digital data to output as the second image.

5. The optical imaging system of claim 4, wherein the image processing unit further comprises an image merging unit merging the first and second images to display the merged image on a single monitor.

6. The optical imaging system of claim 5, wherein, when the first image is a general image representing a shape of the object or distribution of signal intensity of the object, the second image is a fluorescence image enlarging and representing a desired target portion of the object.

7. The optical imaging system of claim 1, wherein the camera is a charge coupled device camera.

8. An optical imaging system using multiple light sources, comprising:
    a first light source generating a white light modulated with a first frequency;
    a second light source generating a fluorescence light modulated with a second frequency, which is different from the first frequency;
    a charge coupler device camera simultaneously detecting multiple lights output from an object after the white light and the fluorescence light are illuminated on the object and outputting multiple image detecting signals, the multiple image detecting signals including a first reflection light of the white light that is reflected on a surface of the object, a second reflection light of the fluorescence light that is reflected on said surface of the object, and a third reflection light of the fluorescence light that is reflected on a desired target portion inside the object;

an optical filter removing the second reflection light of the fluorescence light from the multiple image detecting signals after detection by the charge coupler device camera; and a digital signal processing unit for separating, from the multiple image detecting signals without the removed second reflection light, a first image representing a shape of the object or distribution of signal intensity of the object and a second image representing the desired target portion inside the object.

9. The optical imaging system of claim 8, wherein the fluorescence light is a near infrared modulated wave.

10. The optical imaging system of claim 8, wherein the digital signal processing unit comprises:
an analog-to-digital converter converting the multiple image detection signals into digital data;
a low pass filter low-pass-filtering the digital data to output as the first image; and
a band pass filter band-pass-filtering the digital data to output as the second image.

11. The optical imaging system of claim 8, further comprising an image merging unit merging the first and second images to display the merged image on a single monitor.

12. The optical imaging system of claim 11, further comprising an amplifier amplifying the second image before the second image is merged with the first image.

13. The optical imaging system of claim 11, wherein the white light is a continuous wave.

14. A driving control method of an optical imaging system using multiple light sources, comprising:
illuminating an object with a white light modulated with a first frequency to obtain a first emission light;
inputting the first emission light to a single camera to generate a first image detecting signal;
illuminating the object with a fluorescence light modulated with a second frequency which is different from the first frequency to obtain a second emission light;
simultaneously detecting multiple emission lights that the first and second emission lights are merged through the single camera to generate multiple image detecting signals, the multiple image detecting signals including a first reflection light of the white light that is reflected on a surface of the object, a second reflection light of the fluorescence light that is reflected on said surface of the object, and a third reflection light of the fluorescence light that is reflected on a desired target portion inside the object;
removing the second reflection light of the fluorescence light from the multiple image detecting signals after said simultaneously detecting; and
obtaining a first image representing a shape of the object or distribution of signal intensity of the object from the first reflection light and a second image representing the desired target portion inside the object from the third reflection light.

15. The driving control method of claim 14, further comprising reconfiguring the obtained first and second images and mapping the reconfigured images to one image.

16. The driving control method of claim 14, wherein the separating of the first and second images comprises:
converting the multiple image detecting signals into digital data;
low-pass-filtering the digital data to output as the first image; and
band-pass-filtering the digital data to output as the second image.

17. The driving control method of claim 14, further comprising amplifying the second image.

18. An optical imaging system using multiple light sources, comprising:
a first light source generating a white light modulated with a first frequency;
a second light source generating a fluorescence light modulated with a second frequency which is different from the first frequency;
a charge coupled device camera simultaneously detecting emitted multiple emission lights after the white and fluorescence lights are illuminated on a diagnosis portion to output multiple image detecting signals;
an analog-to-digital converter converting the multiple image detecting signals into digital data;
a first image output unit low-pass-filtering the digital data to output a general image representing a shape of the diagnosis portion or distribution of signal intensity of the diagnosis portion; and
a second image output unit band-pass-filtering the digital data to output a fluorescence image representing a desired target portion of the diagnosed portion.

* * * * *